United States Patent [19]
Marker et al.

[11] Patent Number: 5,324,866
[45] Date of Patent: Jun. 28, 1994

[54] INTEGRATED PROCESS FOR PRODUCING DIISOPROPYL ETHER FROM ISOPROPYL ALCOHOL

[75] Inventors: Terry L. Marker, Warrenville; Laura E. Kempf, Deerfield, both of Ill.

[73] Assignee: UOP, Des Plaines, Ill.

[21] Appl. No.: 36,008

[22] Filed: Mar. 23, 1993

[51] Int. Cl.$^5$ .................. C07C 41/06; C07C 29/04
[52] U.S. Cl. .................. 568/697; 568/897; 568/899
[58] Field of Search .................. 568/697, 897, 899

[56] References Cited

U.S. PATENT DOCUMENTS

| | | | |
|---|---|---|---|
| 4,214,107 | 7/1980 | Chang et al. | 568/897 |
| 4,499,313 | 2/1985 | Okumura et al. | 568/897 |
| 4,857,664 | 8/1989 | Huang et al. | 568/695 |
| 4,906,787 | 3/1960 | Huang et al. | 568/697 |
| 4,935,552 | 6/1990 | Child et al. | 568/695 |
| 5,102,428 | 4/1992 | Owen et al. | 44/448 |
| 5,144,086 | 9/1992 | Harandi et al. | 568/698 |

*Primary Examiner*—Howard T. Mars
*Attorney, Agent, or Firm*—Thomas K. McBride; John F. Spears, Jr.; Reginald K. Taylor

[57] ABSTRACT

The present invention is an integrated isopropyl alcohol (IPA) and diisopropyl ether (DIPE) process. In this process, IPA, substantially free of DIPE, is formed in a hydration reactor by reacting an olefinic feedstock with water in a hydration reactor. The effluent from the hydration reactor is then contacted in a first separation unit with DIPE which was made in an etherification reactor. The resulting mixture is then passed to a second separation unit to separate the IPA from the DIPE product. The IPA is then fed to the etherification reactor to produce DIPE.

16 Claims, 1 Drawing Sheet

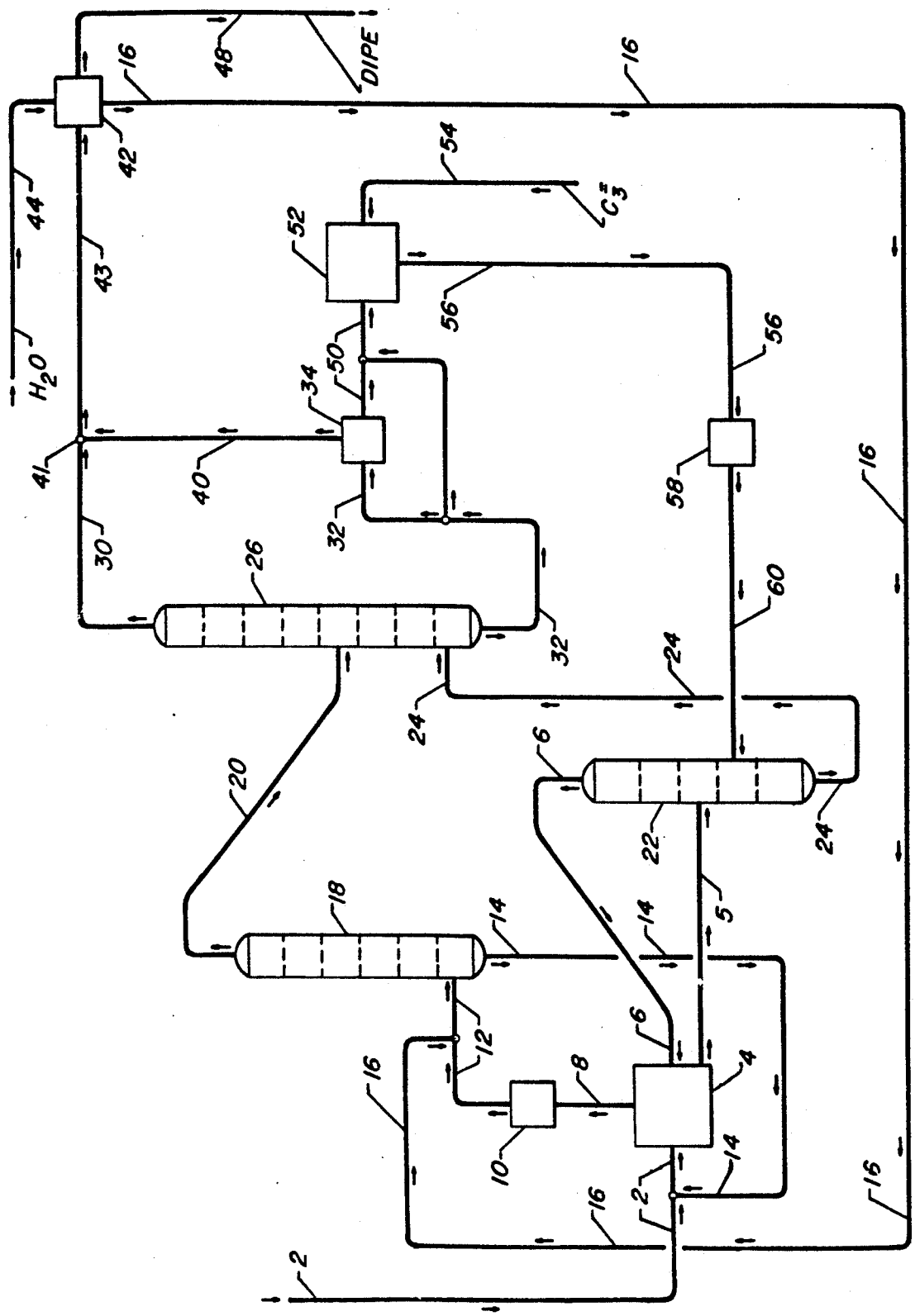

INTEGRATED PROCESS FOR PRODUCING DIISOPROPYL ETHER FROM ISOPROPYL ALCOHOL

FIELD OF THE INVENTION

The present invention relates to a process for producing diisopropyl ether (DIPE) from isopropyl alcohol (IPA). More specifically, the present invention involves an integrated process that first produces IPA and then reacts the IPA with propylene to produce a diisopropyl ether.

BACKGROUND OF THE INVENTION

The need to eliminate lead-based octane enhancers in gasoline has provided an incentive for the development of processes to produce high octane gasolines blended with lower aliphatic octane boosters. Supplementary fuels are being examined by the petroleum refining industry. Lower molecular weight alcohols and ethers, such as isopropyl alcohol (IPA) and diisopropyl ether (DIPE), are in the boiling range of gasoline fuels and are known to have a high blending octane number. They are also useful as octane enhancers. In addition, by-product propylene from which IPA and DIPE can be made is usually available in a fuels refinery, typically as a $C_3$ aliphatic stream which is rich in both propylene and propane.

The preparation of DIPE from propylene chemically proceeds by two sequential reactions where propylene is first hydrated to IPA (1) followed by reaction of the alcohol with the olefin (2) or bimolecular reaction of the alcohol (3) (Williamson synthesis) according to the equations,

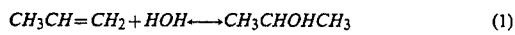

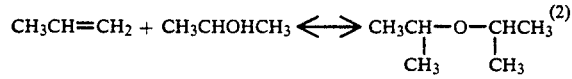

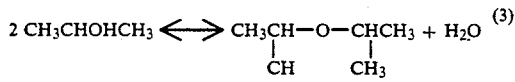

When DIPE is produced via reaction (3), twice as much IPA is required than when DIPE is produced via reaction (2). Since hydration reactions, for example reaction (1), are generally more difficult to perform than etherification reactions, the production rate of the alcohol limits the overall sequence and it is desirable to limit the formation of DIPE from reaction (3) and increase the formation of DIPE from reaction (2). Side reactions that can occur in this process are the reaction of propylene with itself to make $C_6$ olefins and the reaction of $C_6$ olefins with propylene to make $C_9$ olefins. These reactions are considered undesirable since they result in low value polygasoline with low octane and no oxygen content.

The synthetic production of IPA and DIPE is well known. Among the earliest processes for the production of IPA and DIPE were the so-called indirect hydration processes. In the indirect hydration process, a selected olefin feed is absorbed in a concentrated sulfuric acid stream to form an extract containing the corresponding alkyl ester of the sulfuric acid. Thereafter, water is admixed with the ester-containing extract to hydrolyze the ester and to form the desired alcohol and ether which are then recovered, generally by stripping with steam or some other heating fluid. A diluted sulfuric acid stream is thereby produced. This acid stream is then generally treated to concentrate the sulfuric acid stream for recycle to the absorption stage.

In the indirect hydration process, the use of sulfuric acid as a catalyst presents certain problems. First, severe corrosion of process equipment can occur. Second, separating the produced ether from the sulfuric acid can be difficult. Third, a substantial quantity of waste sulfuric acid is produced in the concentration of the catalyst for recovery. Because of these problems, it has been found that the process of synthesizing DIPE by using concentrated sulfuric acid is not commercially viable. Clearly, there was a need for a more direct manner of bringing about the hydration reaction.

This need was addressed by so-called direct hydration processes using solid catalysts. In the direct hydration process, an olefinic hydrocarbon such as propylene is reacted directly with water over a solid hydration catalyst to produce an intermediate IPA stream from which the product DIPE can be formed. Development work using direct hydration focuses on the use of solid catalysts such as active charcoal, clays, resins and zeolites. Examples of olefin hydration processes which employ zeolite catalysts as the hydration catalyst can be found in U.S. Pat. Nos. 4,214,107, 4,499,313, 4,857,664 and 4,906,187.

The use of zeolites as hydration catalysts has the disadvantage of being expensive in comparison to other catalysts, for example, ion exchange resin catalysts. Also, in comparison to ion exchange resin catalysts zeolites do not operate as well at the relatively low temperatures required for hydration and etherification. Furthermore, zeolites have a strong tendency to form DIPE from reaction (3) instead of reaction (2). They also have a strong tendency to produce substantial amounts of undesirable polygasoline from the reaction of propylene with itself.

In many of the direct hydration processes developed by the refining industry, the hydration reactor is operated to produce both IPA and DIPE. In other words, the hydration of olefins to IPA and the etherification of IPA to DIPE occurs in a single reactor. After separation, the IPA is then recycled to the hydration reactor to produce additional DIPE. For example, in U.S. Pat. No. 5,102,428 (issued to Owen et al.) a $C_3$ hydrocarbon feed stream comprising propylene and propane is fed along with water to a single hydration/etherification reactor containing an acidic catalyst. Both hydration and etherification reactions occur in this single reactor. The reactor effluent containing DIPE, IPA and propylene is then passed to a high pressure separator/extractor wherein the effluent is contacted by water to remove a substantial amount of the IPA. The resulting stream is flashed to remove propylene and fractionated to remove the remaining IPA. The aqueous IPA stream and the IPA recovered from fractionation are recycled to the hydration/etherification reactor for reuse. Unconverted propylene is polymerized to form polygasoline using a metallosilicate catalyst rather than recycled to the hydration/etherification reactor to produce additional IPA. This is highly undesirable since it limits the oxygenate production and produces substantial amounts of polygasoline which has low octane.

Using a single reactor for hydration and etherification can present a problem because the conversion of propylene and water to IPA takes place at a higher temperature than the conversion of IPA to DIPE. By having both reactions take place in a single reactor, the conversion of IPA to DIPE must occur at a higher temperature than desired and the conversion of IPA to DIPE is decreased.

Some direct hydration processes use two reactors so that any unreacted IPA formed in the first reactor can be sent to a second reactor to further etherify the IPA. For example, in U.S. Pat. No. 4,935,552, propylene, water and IPA are introduced to a first reactor containing a hydration/etherification catalyst to form an effluent which consists of IPA, DIPE and unreacted reactants. The effluent is then flashed to remove propylene and extracted with water to transfer the IPA to the aqueous phase. A portion of the resulting hydrocarbon phase containing high purity DIPE is recycled to the first reactor in order to control the temperature. This is undesirable since recycling a product in an equilibrium-limited reaction will reduce conversion of the reactants, thereby limiting production of IPA and DIPE. The aqueous IPA phase is passed to a second reactor (catalytic distillation unit) where additional etherification of the IPA to form DIPE takes place. In this second reactor, DIPE is made exclusively by reaction (3) since the propylene has all been removed. This means the first reactor has to make twice as much IPA to make the same amount of DIPE.

U.S. Pat. No. 5,144,086 (issued to Harandi et al.) discloses an integrated IPA and DIPE process that has two separate reactors, one for the exclusive formation of IPA and the other dedicated to etherification. In this process, propylene and water are introduced to a first hydration reactor containing an acidic hydration catalyst to produce an IPA-containing effluent that is substantially free of DIPE. After separating the effluent stream to remove the propylene and propane, the IPA-containing stream is passed to an etherification reactor containing a zeolite catalyst to produce an etherification effluent that contains DIPE, water and propylene. This process produces DIPE by reaction (3) rather than reaction (2) and therefore requires twice as much IPA to be made. The effluent from the etherification reactor is then fractionated to produce the DIPE product. This process suggests using one separation zone (distillation column) to remove C$_3$ hydrocarbons and water from the intermediate IPA stream and another separation zone to remove C$_3$ hydrocarbons and water from the DIPE product stream, resulting in a considerable addition to the capital expense of the integrated process.

There is a need for an integrated IPA and DIPE process which utilizes common separation zones to remove C$_3$ hydrocarbons and water from the IPA and DIPE streams, and which maximizes conversion in each stage, minimizes formation of DIPE from dehydration (reaction 3), and minimizes polygasoline formation. And it is the object of this invention to fill this need.

SUMMARY OF THE INVENTION

It has been discovered that the aforementioned object can be accomplished using common separation zones in an integrated IPA and DIPE process to remove unreacted hydration products (C$_3$ hydrocarbons and water) from an intermediate IPA stream and the DIPE product stream. This maximizes the conversion in each reactor so that less recycle material is needed. Furthermore, this process minimizes undesirable side reactions that form polygasoline and maximizes DIPE formation from reaction (2) rather than reaction (3), thereby minimizing the required size of the IPA reactor. The benefits result in a reduction in both capital and utility cost for the integrated process.

The present invention is an integrated process for the production of diisopropyl ether which process comprises the steps of: contacting an olefinic feedstock with water in a hydration zone in the presence of a hydration catalyst under hydration conditions to produce a hydration zone effluent stream substantially free of diisopropyl ether; contacting at least a portion of the hydration zone effluent stream with at least a portion of an etherification zone effluent stream and separating the hydration and etherification zone effluent streams in a first separation zone to produce an olefin-containing stream and a first separation zone effluent stream; passing at least a portion of the first separation zone effluent stream to a second separation zone to produce an ether product stream comprising diisopropyl ether and a second separation zone effluent stream comprising isopropyl alcohol; passing the second separation zone effluent stream and an olefinic hydrocarbon stream to an etherification zone and contacting the isopropyl alcohol with the olefinic hydrocarbon stream in the presence of an etherification catalyst under etherification conditions to form the etherification zone effluent stream; and passing the etherification zone effluent stream to the first separation zone.

In one embodiment, the present invention is an integrated process for the production of diisopropyl ether which process comprises the steps of: contacting an olefinic hydrocarbon with water in a hydration zone in the presence of an ion exchange resin hydration catalyst under hydration conditions to produce a hydration zone effluent stream substantially free of diisopropyl ether; contacting at least a portion of the hydration zone effluent stream with at least a portion of an etherification zone effluent stream and separating the hydration and etherification zone effluent streams in a first separation zone comprising a distillation column to produce an olefin-containing stream and a first separation zone effluent stream; passing at least a portion of the first separation zone effluent stream to a second separation zone comprising a distillation column to produce an ether product stream comprising diisopropyl ether and a second separation zone effluent stream comprising isopropyl alcohol; passing at least a portion of the second separation zone effluent stream and an olefinic hydrocarbon stream to an etherification zone and contacting the isopropyl alcohol with the olefinic hydrocarbon in the presence of an ion exchange resin etherification catalyst under etherification conditions to form the etherification zone effluent stream; passing the etherification zone effluent stream to a sulfur treatment zone; and passing the resulting etherification zone effluent stream to the first separation zone.

In another embodiment, the present invention is an integrated process for the production of diisopropyl ether which process comprises the steps of: contacting an olefinic hydrocarbon feedstock comprising a mixture of propane and propylene with water in a hydration zone in the presence of an ion exchange hydration catalyst under hydration conditions to produce a hydration zone effluent stream substantially free of diisopropyl ether; contacting at least a portion of the hydration zone effluent stream with at least a portion of an etherification zone effluent stream and separating the hydration and etherification effluent streams in a first separation zone comprising a distillation column to produce an olefin-containing stream and a first separation zone effluent stream; passing at least a portion of the first separation zone effluent stream to a second separation zone comprising a distillation column to produce an ether product stream comprising diisopropyl ether and a second separation zone effluent stream comprising isopropyl alcohol; passing at least a portion of the second separation zone effluent stream to a polygasoline hydrocarbon removal zone comprising a distillation column; passing at least a portion of the second separation zone effluent stream and propylene to an etherification zone and contacting the isopropyl alcohol with the propylene in the presence of an ion exchange resin etherification catalyst under etherification conditions to form the etherification zone effluent stream; passing at least a portion of the etherification zone effluent stream to a sulfur treatment zone containing an adsorbent capable of removing $SO_3$ from the etherification zone effluent stream; and passing at least a portion of the resulting etherification zone effluent stream to the first separation zone.

BRIEF DESCRIPTION OF THE DRAWING

The FIG. is a schematic representation of one embodiment of the present invention.

DESCRIPTION OF THE PREFERRED EMBODIMENT

In the present invention, an olefinic hydrocarbon feedstock is contacted with water in a hydration zone in the presence of a hydration catalyst under hydration conditions to produce a hydration zone effluent stream that is substantially free of diisopropyl ether.

The olefinic hydrocarbon feedstock comprises propylene or a refinery $C_3$ hydrocarbon stream comprising propylene and propane. Suitable sources for the olefinic hydrocarbon feedstock include, but are not limited to, gas plant off-gas containing propylene, naphtha cracker off-gas containing light olefins, and refinery fluidized catalytic cracked (FCC) propane/propylene streams. It is preferred that the olefinic hydrocarbon feedstock have a propylene concentration in the range of about 50-92 mole %, depending upon whether the propylene is being fed to the hydration zone or the etherification zone. Increasing the propylene purity of the olefinic hydrocarbon feedstock can be accomplished through fractionation or any other processes known to those skilled in the art. For example, the olefinic hydrocarbon feedstock can comprise greater than 92 mole % propylene to the hydration zone and greater than 72 mole % to the etherification zone. In another example, the olefinic feedstock can comprise 92 mole % to both the hydration and etherification zones.

The hydration catalyst can be any known hydration catalyst including, but not limited to, ion exchange resin and zeolite catalysts. The preferred catalyst is a strongly acidic cation exchange of the sulfonic acid-type resin derived from styrene, phenolsulfonic acid-type resin and the like. The sulfonic acid type ion exchange resin derived from styrene is obtained by copolymerizing styrene with a polyunsaturated compound such as divinylbenzene to thereby yield a resin, and then sulfonating the resin thus obtained.

Shape-selective acidic zeolite catalysts can also be used as hydration catalysts. Two categories of zeolites are useful, namely the intermediate pore size variety, for example, ZSM-5, and the large pore size variety as represented by, for example, Y, Beta and ZSM-12 zeolites.

An essential feature of the present invention is the use of hydration conditions that render the hydration zone effluent substantially free of diisopropyl ether. Substantially free is intended to mean less than about 10 mole % diisopropyl ether, preferably less than about 5 mole %. Suitable hydration conditions include a temperature of about 50°–450° F., preferably about 280°–350° F., a pressure of about 100–3500 psi, preferably 1000–1600 psi, and a water to olefin ratio of about 0.1:1 to 30:1, preferably about 5:1 to 16:1.

The hydration process can be carried out under dense phase, liquid phase, vapor phase or mixed vapor-liquid phase conditions in a batch or continuous manner. With respect to the reactor, a stirred tank or fixed bed reactor can be employed. The flow of reactants and products can be trickle-bed, liquid-upflow, liquid-downflow, countercurrent, or cocurrent. A suitable liquid hourly space velocity is about 0.1 to 20, preferably about 0.1 to 2 when operating in the continuous mode. The preferred embodiment of the hydration zone is trickle-bed. A suitable method and reactor for operating the hydration zone is described in U.S. Pat. Nos. 4,281,206 and 4,579,984.

In the trickle-bed reactor design, separation of water and hydrocarbons can occur near the bottom of the reactor. The water falls into a lower phase and the hydrocarbons rise to an upper phase. The water phase can contain a substantial amount of IPA. In a preferred embodiment, additional separation is performed on the water phase to remove additional hydrocarbons by passing the water phase to a separation vessel and reducing the pressure to remove dissolved hydrocarbons. The water coming from the separation vessel can be passed to a water treatment zone for the removal of sulfurous acid that can originate from the use of an ion exchange resin as the hydration catalyst. The water leaving the water treatment zone then goes to a water recovery column where it is separated from IPA and DIPE. The water can be recycled back to the hydration zone. The IPA and DIPE can be sent to a second separation zone that will be described in more detail later.

The hydrocarbon portion of the hydration zone effluent is introduced to a first separation zone where such effluent is contacted with an etherification zone effluent stream which is produced from an etherification zone positioned downstream in the integrated process of the present invention. The first separation zone produces an olefin-containing stream comprising a mixture of propylene and propane and a first separation zone effluent stream comprising isopropyl alcohol, diisopropyl ether, and a small amount of water. Preferably, the first separation zone is a fractionation tower operated at conditions suitable for removing a mixture of propylene and propane from the hydration and etherification zone effluent streams.

In accordance with the present invention, at least a portion of the first separation zone effluent stream is passed to a second separation zone. The overhead from the water recovery column containing IPA, DIPE, and a small amount of water is also passed to the second separation zone. An ether product stream comprising diisopropyl ether and a second separation zone effluent stream comprising isopropyl alcohol are produced in the second separation zone. The second separation zone is operated at conditions sufficient to separate a substantial amount of the diisopropyl ether from the isopropyl alcohol. As used herein, substantial is defined as greater than about 75-88 mole % of the IPA entering the second separation zone. In a preferred embodiment, the ether product stream, which also contains a small amount of isopropyl alcohol, is passed to a water wash zone to remove any remaining isopropyl alcohol.

The second separation zone effluent stream is then passed to an etherification zone wherein it is reacted with an added olefinic-containing stream in the presence of an etherification catalyst under etherification conditions.

The etherification catalyst can be any known etherification catalyst including, but not limited to, ion exchange resin and zeolite catalysts. The preferred catalyst is a strongly acidic cation exchange resin of the sulfonic acid-type resin derived from styrene, phenolsulfonic acid-type resin and the like. Shaped-selective acidic zeolite catalysts can also be used. Two categories of zeolites are useful, namely, the intermediate pore size variety, for example, ZSM-5, and the large pore size variety as represented, for example, Y, Beta and ZSM-12 zeolites. Because in the present invention the etherification and hydration zones are separate, the etherification catalyst can be specifically chosen to suit etherification conditions rather than hydration conditions.

Suitable etherification conditions include a temperature of about 90°-200° F., a pressure of about 100-1200 psi, preferably about 700-1000 psi, and an olefin to isopropyl alcohol ratio of about 1:1 to 2:1. It is important to keep the olefin to isopropyl alcohol ratio in this range to avoid reaction (3) and promote etherification reaction (2).

Etherification can be carried out under dense phase, liquid phase, vapor phase or mixed vapor-liquid phase conditions in batch or continuous manner. With respect to the etherification reactor, a stirred tank reactor or fixed bed reactor can be employed. The flow of reactants and products can be trickle-bed, liquid-upflow, liquid-downflow, countercurrent, or cocurrent, a liquid hourly space velocity of about 0.1 to 20, preferably about 0.1 to 2 when operating in the continuous mode. In a preferred embodiment, the etherification reactor can be a liquid phase fixed-bed reactor with recirculation of cooled etherification zone effluent for temperature control.

In accordance with the process of the present invention, the effluent from the etherification zone is recycled to the first separation zone.

In a preferred embodiment, the etherification effluent is passed to a sulfur treatment zone prior to being recycled to the first separation zone. The sulfur treatment zone contains an adsorbent for selectively removing $SO_3$ from the etherification zone effluent. $SO_3$ can be generated in the etherification zone when an acidic ion exchange resin catalyst is used.

The following example is based on a design for a commercial scale unit. Referring to the figure, water is fed into IPA reaction zone 4 via line 2 at a flow rate of 1000 lb moles/hr. Propylene enters into IPA reaction zone 4 via line 6 at a flow rate of about 1608 lb moles/hr. Passing the propylene of stream 6 to a fractionation column (not shown) which removes propane from the system can increase the purity of the propylene. In IPA reaction zone 4, water is reacted with propylene to produce IPA. The IPA reaction zone 4 contains a separation vessel for the separation of water and the hydrocarbon phase and is operated at hydration conditions sufficient to produce an IPA reaction zone effluent stream substantially free of DIPE. The IPA reaction conditions include a temperature of about 300° F. and a pressure of about 1500 psia. The IPA reaction zone effluent stream 5, which has a composition as shown in Table 1, is fed into first separation zone 22 via line 5.

First separation zone 22 comprises a fractionation column which removes $C_3$ hydrocarbons from the hydration and etherification zone effluents which enter the first separation zone 22 through lines 5 and 60, respectively. Etherification zone effluent stream 60 enters first separation zone 22 via line 60 at a flow rate of about 1677 lb moles/hr and a composition as shown in Table 1. The etherification effluent stream originates from DIPE reaction zone 52. The second separation zone 26 receives the DIPE/IPA stream via line 24 at a flow rate of 665 lb moles/hr. DIPE/IPA stream 24 has a composition as shown in Table 1.

A water/IPA stream exits IPA reaction zone 4 in line 8. The water/IPA stream is passed to water treatment zone 10 via line 8. Water treatment zone 10 contains a solid adsorbent for removing impurities such as $SO_3$ and chloride. After treatment, the water/IPA stream is passed to water recovery column 18 through line 12. Water recovery column 18 is operated at an average temperature of about 250°-319° F. and an average pressure of about 78-89 psia. A water-containing stream exits the bottom of water recovery column 18 and enters IPA reaction zone 4 through line 14. An IPA/water mixture having the composition shown in Table 1 is removed from the top of water recovery tower 18 in line 20. The IPA/water mixture enters second separation zone 26 at a flow rate of about 976 lb moles/hr.

In second separation zone 26, DIPE product is separated from IPA. Second separation zone 26 is operated at an average temperature of about 120°-221° F. and an average pressure of about 28-35 psia. Accordingly, an ether product stream having a composition as shown in Table 1 is removed from the top of second separation zone 26 via line 30 at a flow rate of about 719 lb moles/hr. The ether product stream is fed to water wash zone 42 via line 30. In water wash zone 42, the ether product stream comes in contact with water (which enters through stream 44) in a countercurrent fashion. The IPA, being more soluble in water than DIPE, is transferred into the water phase. The water phase exits water wash zone 42 through stream 16. Stream 16 is recycled to water recovery column 18. Also exiting the water wash zone 42 by line 48 is a high purity DIPE product stream.

Exiting the bottom of the second separation zone 26 in line 32 is an IPA-containing stream having a composition as shown in Table 1. At least a portion of stream 32 is first fed to polygasoline removal zone 34 and then to DIPE reactor 52 via line 50. The polygasoline removal zone 34 is comprised of a fractionation column (not shown) that removes the heavier polygasoline components from the IPA-containing stream that is to be fed to the DIPE reactor 52. The polygasoline exits the polygasoline removal zone 34 via line 40 and admixes with the ether product stream at junction 41. The resulting stream 43 is passed on to the water wash zone 42.

The IPA-containing stream is passed to DIPE reactor 52 via line 50. Also entering the DIPE reactor 52 via line 54 is fresh propylene. In DIPE reactor 52, propylene is reacted with IPA to form DIPE in the presence of an ion exchange resin catalyst under etherification conditions. Exiting DIPE reactor 52 through line 56 is an etherification zone effluent stream comprising IPA, DIPE, and propylene. This stream is first sent to a sulfur treatment zone 58 for removal of $SO_3$. The resulting etherification effluent stream, having composition as shown in Table 1, is then recycled to the first separation zone 22 where the etherification effluent stream comes into contact with the IPA-containing stream that is produced in IPA reaction zone 4.

TABLE 1

| Component | | Stream No. | | | | | |
|---|---|---|---|---|---|---|---|
| | | 5 | 20 | 24 | 30 | 32 | 60 |
| Propane | mole frac. | 0.2001 | 0.0003 | 0.0000 | 0.0004 | 0.0000 | 0.2190 |
| i-Butane | mole frac. | 0.0000 | 0.0000 | 0.0005 | 0.0005 | 0.0000 | 0.0057 |
| Propene | mole frac. | 0.5636 | 0.0017 | 0.0000 | 0.0023 | 0.0000 | 0.3793 |
| $H_2O$ | mole frac. | 0.1550 | 0.3139 | 0.0000 | 0.1554 | 0.0000 | 0.0132 |
| 2-$C_3$ol | mole frac. | 0.0592 | 0.6513 | 0.3467 | 0.2161 | 0.9775 | 0.1277 |
| di-i-Ether | mole frac. | 0.0220 | 0.0328 | 0.6466 | 0.6252 | 0.0167 | 0.2527 |
| 1-Nonene | mole frac. | 0.0000 | 0.0000 | 0.0063 | 0.0000 | 0.0058 | 0.0025 |

What is claimed is:

1. An integrated process for the production of diisopropyl ether which process comprises the steps of:
   (a) contacting an olefinic hydrocarbon comprising propylene with water in a hydration zone in the presence of a hydration catalyst under hydration conditions to produce a hydration zone effluent stream substantially free of diisopropyl ether;
   (c) contacting at least a portion of said hydration zone effluent stream with at least a portion of a hereinafter characterized etherification zone effluent stream and separating the hydration and etherification zone effluent streams in a first separation zone to produce an olefin-containing stream and a first separation zone effluent stream;
   (c) passing at least a portion of said first separation zone effluent stream to a second separation zone to produce an ether product stream comprising diisopropyl ether and a second separation zone effluent stream comprising isopropyl alcohol;
   (d) passing said second separation zone effluent stream and an olefinic hydrocarbon stream, comprising propylene, to an etherification zone and contacting said isopropyl alcohol with said olefinic hydrocarbon in the presence of an etherification catalyst under etherification conditions to form said etherification zone effluent stream; and
   (e) passing at least a portion of said etherification zone effluent stream to said first separation zone.

2. The method of claim 1 wherein said etherification zone effluent stream is passed through a sulfur treatment zone.

3. The method of claim 2 wherein said sulfur treatment zone comprises an adsorbent capable of removing $SO_3$ from said etherification zone effluent stream.

4. The method of claim 1 wherein said second separation zone effluent stream is passed through a polygasoline hydrocarbon removal zone.

5. The method of claim 4 wherein said polygasoline hydrocarbon removal zone comprises a distillation column.

6. The method of claim 1 wherein said first and second separation zones each comprise a distillation column. an ion exchange resin.

7. The method of claim 1 wherein said olefinic feedstock comprises propylene.

8. The method of claim 7 wherein said olefinic feedstock further comprises a propylene and propane mixture.

9. The method of claim 1 wherein said hydration catalyst comprises an ion exchange resin.

10. The method of claim 1 wherein said etherification catalyst comprises an ion exchange resin.

11. An integrated process for the production of diisopropyl ether which process comprises the steps of:
   (a) contacting an olefinic hydrocarbon comprising propylene with water in a hydration zone in the presence of an ion exchange resin hydration catalyst under hydration conditions to produce a hydration zone effluent stream substantially free of diisopropyl ether;
   (b) contacting at least a portion of said hydration zone effluent stream with at least a portion of an hereinafter characterized etherification zone effluent stream and separating said hydration and etherification zone effluent streams in a first separation zone comprising a distillation column to produce an olefin-containing stream and a first separation zone effluent stream;
   (c) passing at least a portion of said first separation zone effluent stream to a second separation zone comprising a distillation column to produce an ether product stream comprising diisopropyl ether and a second separation zone effluent stream comprising isopropyl alcohol;
   (d) passing at least a portion of said second separation zone effluent stream, comprising propylene, and an olefinic hydrocarbon stream to an etherification zone and contacting said isopropyl alcohol with said olefinic hydrocarbon in the presence of an ion exchange resin etherification catalyst under etherification conditions to form said etherification zone effluent stream;
   (e) passing at least a portion of said etherification zone effluent stream to a sulfur treatment zone; and
   (f) passing the resulting etherification zone effluent stream to said first separation zone.

12. The method of claim 11 wherein said sulfur treatment zone comprises an adsorbent capable of removing $SO_3$ from said etherification zone effluent.

13. The method of claim 11 wherein said second separation zone effluent stream is passed through a polygasoline hydrocarbon removal zone.

14. The method of claim 13 wherein said polygasoline hydrocarbon removal zone comprises a distillation tower.

15. The method of claim 11 wherein said olefinic feedstock further comprises a propylene and propane mixture.

16. An integrated process for the production of diisopropyl ether which process comprises the steps of:

(a) contacting an olefinic hydrocarbon feedstock comprising a mixture of propane and propylene with water in a hydration zone in the presence of an ion exchange hydration catalyst under hydration conditions to produce a hydration zone effluent stream substantially free of diisopropyl ether;

(b) contacting at least a portion of said hydration zone effluent stream with at least a portion of an etherification zone effluent stream and separating the said hydration and etherification effluent streams in a first separation zone comprising a distillation column to produce an olefin-containing stream and a first separation zone effluent stream;

(c) passing at least a portion of said first separation zone effluent stream to a second separation zone comprising a distillation column to produce an ether product stream comprising diisopropyl ether and a second separation zone effluent stream comprising isopropyl alcohol;

(d) passing said second separation zone effluent stream to a polygasoline hydrocarbon removal zone comprising a distillation column;

(e) passing at least a portion of said second separation zone effluent stream and propylene to an etherification zone and contacting said isopropyl alcohol with said propylene in the presence of an ion exchange resin etherification catalyst under etherification conditions to form said etherification zone effluent stream;

(f) passing at least a portion of said etherification zone effluent stream to a sulfur treatment zone containing an adsorbent capable of removing $SO_3$ from said etherification zone effluent stream; and (g) passing at least a portion of the resulting etherification zone effluent stream to said first separation zone.

* * * * *